Figure 3B:
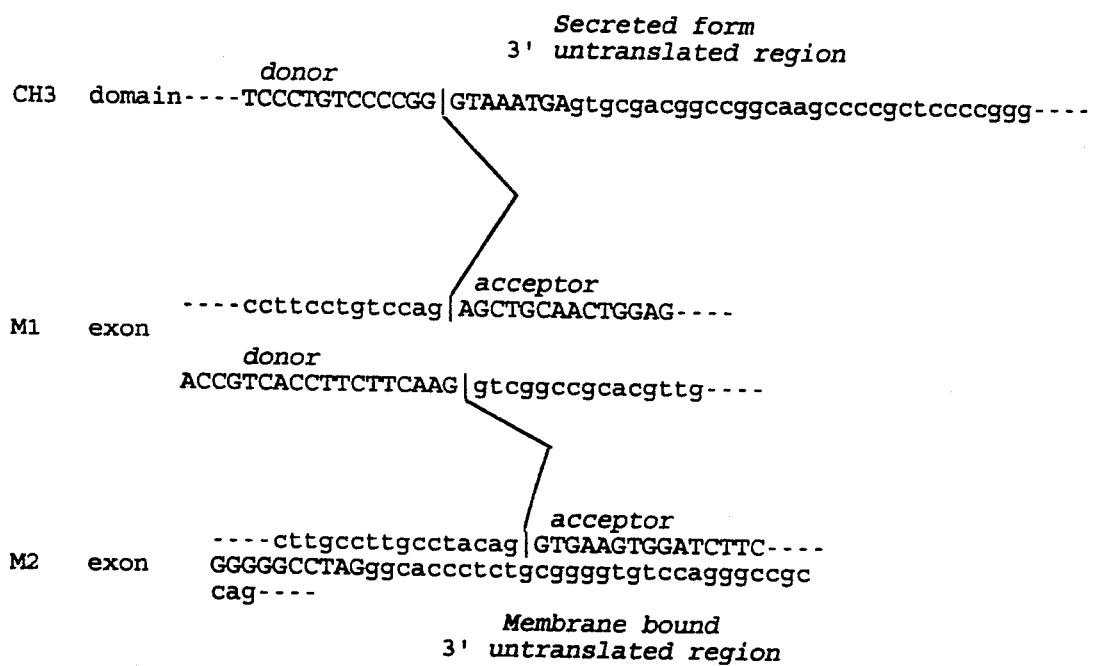

United States Patent [19]

Chang

[11] Patent Number: 5,298,420
[45] Date of Patent: * Mar. 29, 1994

[54] ANTIBODIES SPECIFIC FOR ISOTYPE SPECIFIC DOMAINS OF HUMAN IGM AND HUMAN IGG EXPRESSED OR THE B CELL SURFACE

[75] Inventor: Tse W. Chang, Houston, Tex.

[73] Assignee: Tanox Biosystems, Inc., Houston, Tex.

[*] Notice: The portion of the term of this patent subsequent to Feb. 25, 2009 has been disclaimed.

[21] Appl. No.: 902,449

[22] Filed: Jun. 19, 1992

Related U.S. Application Data

[63] Continuation of Ser. No. 562,201, Aug. 3, 1990, abandoned.

[51] Int. Cl.$^5$ .................... C07K 15/28; C12N 1/21; C12N 5/12; C12P 21/08
[52] U.S. Cl. .................... 435/240.27; 530/387.9; 530/388.73; 530/387.3; 435/69.6; 435/252.3
[58] Field of Search ............. 530/388.73, 387.1, 387.3, 530/387.9; 435/240.27, 69.6, 252.3

[56] References Cited

U.S. PATENT DOCUMENTS 5,091,313 2/1992 Chang ........................... 435/240.27

OTHER PUBLICATIONS

Rincon et al. Immunology 1984, 53:713.
Sevier et al. Clinical Chem. 27(11) 1797–1806 1981.
Morrison et al. PNAS vol. 81 pp. 6851–6855 1984.
Cheng et al. Nature vol. 296 1982 p. 410.
Blattner et al. Nature vol. 307 p. 418 1984.
Riechmann et al. Nature 332:323–327 1988 (applicant's cited art).
Word et al. "The murine immunoglobulin α gene expresses multiple transcripts from a unique membrane exon" (particularly; p. 895, 2nd column) EMBO Journal 2:887–898 (1983).
Manning, D. D., "Heavy Chain Isotope Suppression: A Review of the Immunosuppressive Effects of Heterograms Anti-Ig Heavy Chain Antisera" J. Reticulo. Soc. 18:63–86 (1975).
Manning D. D. et al. "Suppression of Regionic Antibody (IgE) Formation in Mice by Treatment with Anti-U Antiserum" J. Exp. Med. 144:288–293 (1976). Manning
Bazin, H. et al. "Differential Effect of Neonatal Injections of Anti-U or Anti-β Antibodies on the Synthesis of IgM, IgE, IgA, IgG1, IgG2a IgG2b and IgG2c Immunoglobulin Classes" J. Immunol. 121:2083–2087 (1978).
Tahghi Kilani, R. et al. "The Role of Humoral Immunity in Cryptospondium Spp. Intection Studies with B Cell-Depleted Mice" J. Immunol. 145:1571–1576 (1990).

Primary Examiner—Y. Christina Chan
Assistant Examiner—L. Feisee
Attorney, Agent, or Firm—Eric P. Mirabel

[57] ABSTRACT

Membrane anchoring peptides are attached to the C terminal end of the heavy chain of the various immunoglobulin isotypes (IgM, IgD, IgA, IgE, or IgG). The membrane anchoring peptides span the cell membrane lipid bilayer of B cells thereby affixing the associated immunoglobulin to the cell membrane surface. The extracellular segments of these peptides are unique for different isotypes. Epitopes unique to the B cells which produce each isotype are formed, in whole or in part, by these extracellular segments. These membrane-bound immunoglobulin isotype-specific ("migis") extracellular epitopes are not present on the secreted, soluble form of the immunoglobulins, which are not bound to the cell surface by the membrane anchoring peptides. The antibodies of the invention (and other related products) specifically bind to the extracellular migis epitopes of human μ chain, human δ chain, or human γ chain. The B cells which express the isotypes IgM, IgD or IgG are labeled for destruction when bound by such antibodies or products, and can be destroyed by the cytolytic or regulatory mechanisms of the immune system in order to cause immunosuppression.

8 Claims, 6 Drawing Sheets

Figure 1A

| | |
|---|---|
| CCCAGACCAGAGCAAGGTCCTCGCACACGTGAACACTCCTCGGACACAGGCCCCCACGAG | 60 |
| CCCCACGCGGCACCTCAAGGGCCCACGAGCCTCTCGGCAGCTTCTCCACATGCTGACCTG | 120 |
| CTCAGACAAACCCAGCCCTCCTCCTCACAAGGGTTGCCCCTGCAGCCGCCACACACAC | 180 |
| AGGGGATCACACACCACGTCACGTCCCTGCCCTGGCCCAAGCGTTCCCAGTGCCGGCCCT | 240 |
| TCCCTGCAGGCTGGGGTCACATGAGGTGTGGGCTTCACCATCCTCGCTCCTCTGGGCCTC | 300 |
| AGGGAGGGACACGGGAGACGGGGAGCGGGTCCTGCTGAGGCCAGGTCGCTATCTAGGGCC | 360 |
| GGGTGTCTGGCTGAGCCCCGGGGCCAAAGCTGGTGCCCAGGGCGGGCAGCTGTGGGGAGC | 420 |
| TGACCTCAGGACATTGTTGGCCCATCCCGGCCGGGCCCTACATCCTGGGGCCCCGCCACA | 480 |
| GAGGGAATCACCCCCAGAGGCCCAAGCCCAGGGGGACACAGCACTGATCCACCCCCTTCC | 540 |
| TGTCCAGAGCTGCAACTGGAGGAGAGCTGTGCGGAGGCGCAGGACGGGGAGCTGGACGGG | 600 |
| CTGTGGACGACCATCACCATCTTCATCACACTCTTCCTGTTAAGCGTGTGCTACAGTGCC | 660 |
| ACCGTCACCTTCTTCAAGGTCGGCCGCACGTTGTCCCCAGCTGTCCTTGACATTGTCCCC | 720 |
| CATGCCTGTACAAACTGTCTCTGACACTGTCCACAGGCTGTCCCCACCTGTGCCCTGACG | 780 |
| CTGTCCCCCATGCTCTCACAAACTGTCCCTGACATTGTCCCCAATGCTGCCCCCACCTGT | 840 |
| CCAACAGTGTCCCCCAGGCTCTCCCCACATGTCCCCGACACTGTCCCCCATGCTGTCCCC | 900 |
| ATCTGTCCCCAACACTGTCCCCCACCCTGTCCCCCTTTGTCCCCAACACTGTCCCCCACA | 960 |
| GTTTCCACCTGTCCCTGACACTCCCCCATGCTTTCCCCACCTGTCCCTGACACCATCCCC | 1020 |
| CACTGTCCCCATAGTTCCTGGCCTGTCCCCCACGCTGTCCCCTACAGTACCTGGCACTGT | 1080 |
| CCCCCATGCTGTCCCCTCCTGTTATGAAACCCTGTCCCACATGCTGTCCCCACCTGTCCG | 1140 |
| TGACAATATCCCCCACACTGTCCCCACCTGTCCCCGACACTCTCCTCCACGTTGTTCTTA | 1200 |
| CCTAAACCCGACACTTCCTCCATGCTGTCCCACCCATCTCCGACACTGTACCCA | 1254 |

Figure 1B

| | |
|---|---|
| TCCCCTATAATCCCTACACTGTCCCCCACACCGTCCCCTCCTGTATGCACCACTGTCCCC | 60 |
| CATGCTGTCCCCACCTGTCCCTGATGCTGTCCTCCACACATCCCCACCTCTCCCTACACT | 120 |
| GTCCCCATCTCTCCCCAACACTCTCCTCCTCCATGCTGTCCTCAACTGTCCCCAACACTC | 180 |
| TTCCACACTCTGTCTCCACCTGTCCCTGACACTGTCCCCCTACACTGTCCTCACCTGTGT | 240 |
| CTGACACTGTCCCCCACGCTGTCCCCACCTGTCCCTGAACGCTGTCTTCTGTGCTGTCCA | 300 |
| CATGCTGTTGGAGCCCTGGCTCTGCTCTCTATCACCAAGCCTCAGAGCAGGCAGTGGTGA | 360 |
| GGCCATGGCACCTGGGTGGCATGAGGGGCCGGATGGGCCTCAGGGGCAGGGCTGTGGCCT | 420 |
| GCGTGGACTGACGGGTGGGTGGGCCTTGGGGGCAGAGAGGTGGCCTCAGTGCCCTGAGGG | 480 |
| GTGGGTGGGGCTCGGGGGCAGGGCTGTGGCCTCGCTCACCCCTGTGCTGTGCCTTGCCTA | 540 |
| CAG<u>GTGAAGTGGATCTTCTCCTCGGTGGTGGACCTGAAGCAGACCATCATCCCCGACTAC</u> | 600 |
| <u>AGGAACATGATCGGACAGGGGGCCTAG</u>GGCACCCTCTGCGGGGTGTCCAGGGCCGCCCAG | 660 |
| ACCCCACACACCAGCCATGGGCCATGCTCAGCCACCACCCAGGCCACACCTGCCCCCGAC | 720 |
| CTCACCGCCCTCAACCCCATGGCTCTCTGGCCTCGCAGTTGCCCTCTGACCCTGACACAC | 780 |
| CTGACCATAGACGGTCTACCCCAGACCTCCGCCAGTTGGTGCATGCAGGGGCATGGGG | 838 |

Figure 2A

```
γ1   cagcactgaccaccccttcctgtccaGAGCTGCAACTGGAGGAGAGCTGTGCGGAGGCG
γ2   --t-t--------a------------------------------------TGC-----
γ3   ----------------------------------------------------------
γ4   ----------------------------------------------------------

γ1   CAGGACGGGGAGCTGGACGGGCTGTGGACGACCATCACCATCTTCATCACACTCTTCCTG
γ2   --------------------------------C-------------------------
γ3   ----------------------------------------------------------
γ4   ----------------------------------------------------------

γ1   TTAAGCGTGTGCTACAGTGCCACCGTCACCTTCTTCAAGgtcggccgcacgttgtcccca
γ2   C-------------------A-------------------t-----------------
γ3   ----------------------------------------------------------
γ4   C-------------------------------------------------cat-gt--c γ1   gctgtccttga--/ /--cccctgtgctgtgccttgcctacagGTGAAGTGGATCTTCTC
γ2   ------------/ /-------------------------------------------
γ3   ------------/ /-------------------------------------------
γ4   a-c--gg-cct--/ /------------------------------------------

γ1   CTCGGTGGTGGACCTGAAGCAGACCATCATCCCCGACTACAGGAACATGATCGGACAGGG
γ2   ---A----------------G-----------------------------A-G-----
γ3   ---------------------------------T-----------T--G---------
γ4   ---A----------------G-----------------------------AA-G----

γ1   GGCCTAGggcaccctctgcggggtgtccaggg
γ2   --------------------t-----------
γ3   -----------------------.-----c--
γ4   --------------------------------
```

Figure 2B

```
          extracellular segment
γ1    ELQLEESCAEAQDGELDG| LWTTITIFITLFLLSVCYSATVTFFKVKWIFSSVVDLKQTII
γ2    -----------------|----------------------I------------------V
γ3    -----------------|-------------------------------------------
γ4    -----------------|------------------------------------------V

γ1    PDYRNMIGQGA
γ2    -------R---
γ3    -----------
γ4    -------R---
```

Figure 3A

```
         CH3 Domain                        | M1 Exon
......CAGAAGAGCCTCTCCCTGTCCCCGGAGCTGCAACTGGAGGAGAGCTGTGCGGAG GCGCAGGACGGGGAGCTGGACGGGCTGTGGACGACCATCACCATCTTCATCACACTCTTC
                                              | M2 Exon
CTGTTAAGCGTGTGCTACAGTGCCACCGTCACCTTCTTCAAGGTGAAGTGGATCTTCTCC
      | 3' Untranslated region
GCCTAGGGCCACCCTCTGCGGGGTGTCCAGGGCCGGCCCAGACCCCACACACCAGCCATG

GGCCATGCTCAGCCACCACCCAGGCCACACCTGCCCCCGTCCTC......
```

ANTIBODIES SPECIFIC FOR ISOTYPE SPECIFIC DOMAINS OF HUMAN IGM AND HUMAN IGG EXPRESSED OR THE B CELL SURFACE

This is a continuation of copending application Ser. No. 07/562,201 filed on Aug. 3, 1990, now abandoned.

FIELD OF THE INVENTION

The invention relates to suppressing or depleting immunoglobulin-producing B cells by antibody targeting of isotype-specific epitopes expressed on the surface of IgM, IgD and IgG bearing B cells.

BACKGROUND OF THE INVENTION

Monoclonal antibodies, or related products such as monoclonal antibodies conjugated with cytotoxic or cytolytic agents, have a number of therapeutic uses. For example, Monoclonal antibodies (or conjugates and related products) specific for the gp120 envelope protein of human immunodeficiency virus type 1 (HIV-1) can be used in therapy for AIDS or AIDS related complex (ARC), or in prophylactic treatment of seropositive but asymptomatic individuals, or uninfected individuals who have been exposed or are at a high risk of exposure to HIV-1. See U.S. application Ser. No. 07/343,540, filed Apr. 25, 1989. They can also be used to suppress or deplete B cells of a particular isotype for treatment of autoimmune diseases. In rheumatoid arthritis, for example, some autoantibodies of IgM or IgG, known as rheumatoid factors, are produced and bind to autologous IgG. The rheumatoid factors and IgG form immune complexes, which are believed to cause inflammation and tissue damage at the joints and other symptoms of rheumatoid arthritis. See U.S. patent application Ser. No. 07/408,123, filed Sep. 15, 1989. Suppression or depletion of malignant B cells with monoclonal antibodies (or mAb-conjugates) may also be desired in therapy for B cell lymphoma or leukemia. See U.S. application Ser. No. 07/531,787, filed Jun. 1, 1990. Suppressing or depleting the IgE expressing B cells with monoclonal antibodies (or mAb-conjugates) may also be an effective therapy for IgE-mediated allergies. See U.S. application Ser. No. 07/515,604, filed Apr. 27, 1990; published international application PCT/US88/04706.

One problem associated with in vivo administration of monoclonal antibodies and related products arises because monoclonal antibodies are generally animal-derived, and most often, mouse-derived. Murine antibodies are foreign proteins and often evoke an endogenous in vivo immune response which may reduce or destroy their therapeutic effectiveness. In addition, murine antibodies may cause an allergic or hypersensitivity reaction. In therapy, there is a need to readminister the antibody, and this re-administration increases the likelihood that these undesirable immune-related reactions will occur.

One way to ameliorate the problems associated with the in vivo use of a murine antibody is to convert the murine antibody to a "chimeric" antibody, consisting of the variable region of the animal or murine antibody joined to a human constant region. See, e.g., Morrison, S. L. et al. (1984) "Chimeric Human Antibody Molecules: Mouse Antigen-binding Domains with Human Constant Region Domains" *Proc. Natl. Acad. Sci. USA* 81: 6851; Neuberger, M. S. and Rabbits, T. H. "Production of Chimeric Antibodies" PCT Application No. PCT/GB85 00392; Sun, L. K. et al., (1987) *Proc. Natl. Acad. Sci. USA* 84:214; Liu, A. Y. et al., (1987) *J. Immunol.* 139: 3521; Sahagan, B. G. et al., (1986) *J. Immunol.* 137: 1066; Liu, A. Y. et al., (1987) *Proc. Natl. Acad. Sci. USA* 84: 3439. Because chimeric antibodies have a human constant region, and the constant region is the larger region which is believed to be primarily responsible for inducing immune or allergic responses against antibody, chimeric antibodies are less likely to evoke an undesirable immune-related response in humans. Nevertheless, an immune or allergic response against the murine variable region of the chimeric antibody or against the regions at the interface of the constant and variable regions can still result.

It is further noted that other animal or plant derived substances used in therapy or immunization, e.g., animal or plant derived toxins, hormones, and animal sera, are often highly immunogenic or allergenic. In addition, when a monoclonal antibody is conjugated to a toxin, the conjugate may be more immunogenic or allergenic than the toxin or mAb alone. Treatment with any of these agents may not be possible in certain individuals without suppressing the immune/allergic response.

Immunosuppressive agents, such as corticosteroid, cyclosporin, methotrexate, and cyclophosphamide, may be used to suppress such undesirable immune-related responses. However, they can produce serious side-effects. These side-effects result primarily because in addition to suppressing the humoral response, these non-specific agents also act against other immune system components and non-immune system cells.

The desirability of suppressing the immune response when foreign therapeutic proteins are administered has been recognized. See published International Application No. PCT/US89/02166. It has also been recognized that suppressing or depleting B cells by administering anti B-cell antibodies, or fragments or conjugates thereof, may be used in conjunction with administration of conventional mAbs, in order to suppress the undesirable immune responses against the conventional mAbs. See U.S. Pat. No. 4,861,579. However, this patent does not mention the suppression or elimination of B cells on an isotype-specific basis.

SUMMARY OF THE INVENTION

The invention includes isotype-specific monoclonal antibodies, and related products such as mAb fragments, mAb-toxin conjugates, and anti-idiotype antibodies, and the use of such mAbs and related products in suppression or depletion of B cells expressing particular isotypes.

The human immunoglobulin heavy chain isotypes are IgG (having four subclasses), IgA (having two subclasses), IgM, IgD, and IgE. IgG causes opsonization and cellular cytotoxicity and crosses the placenta, IgA functions on the mucosal surface, IgM is most effective in complement fixation, and IgE mediates degranulation of mast cells and basophils. The function of IgD is still not well understood. Resting B cells, which are immunocompetent but not yet activated, express IgM and IgD. Once activated and committed to secrete antibodies these B cells can express any of the five isotypes. The heavy chain isotypes of IgG, IgA, IgM, IgD and IgE are respectively designated the $\gamma$, $\alpha$, $\mu$, $\delta$, and $\epsilon$ chains.

Extending from the C-termini of the immunoglobulin heavy chains are membrane anchoring peptides, which span the cell membrane lipid bilayer and affix the associated immunoglobulin to the cell membrane surface. The extracellular segments of these peptides are unique for different isotypes, but tend to be very similar among different subclasses of a particular isotype. Epitopes unique for the B cells which produce each isotype are formed, in whole or in part, by the extracellular segments of each isotype. specific ("migis") extracellular epitopes are not present on the secreted, soluble form of the immunoglobulins, which are not bound to the cell surface by the membrane anchoring peptides.

The antibodies and other related products of the invention bind to the migis epitopes which are present on the B cell surface of IgM, IgD, or IgG expressing B cells. The B cells which produce any of these isotypes can then be eliminated or controlled by a number of immune cytolytic or regulatory mechanisms. The products of the invention which target migis -δ or migis -μ may be most useful in immuno-suppression because, as noted above, all B cells, irrespective of which of the five isotypes they produce, pass through a stage where they produce IgM and IgD. Thus, the monoclonal antibodies (or mAb-conjugates) of the invention which bind the migis -δ or migis -μ will suppress or deplete B cells which express all five isotypes. It is also noted that IgG is present in vivo in greater concentration than other isotype, and therefore the mAbs and related products of the invention which target migis -γ may also be useful in immunosuppression. Although IgG has four subclasses, the migis segments of all four subclasses have the same sequence, and therefore the anti-migis -γ mAbs of the invention will target all subclasses of IgG.

BRIEF DESCRIPTION OF THE DRAWINGS

FIG. 1A shows the genomic DNA sequence of a segment of human γ-1 chain, the sequence of a first membrane exon which is proposed to encode for the membrane anchoring peptide being underlined, and the flanking nucleotide sequences not being underlined.

FIG. 1B shows the genomic DNA sequence of a segment of human γ-1 chain, the sequence of a second membrane exon which is proposed to encode for the membrane anchoring peptide being underlined, and the flanking nucleotide sequences not being underlined.

FIG. 2A shows the nucleotide sequences of the two membrane exons of human γ-1 chain shown in FIGS. 1A, 1B (some of the flanking sequences are shown by lower case letters), as well as the corresponding nucleotide sequences for human γ-2, γ-3, and γ-4 chains.

FIG. 2B shows the deduced amino acid sequences encoded for by the membrane exons shown in FIG. 1A, the proposed extracellular segment being indicated.

FIG. 3A shows the sequence of a segment of cDNA of human γ-1 chain from mRNA of IM9 cells, linking the CH3 domain to the membrane exon shown in FIG. 1A, to the membrane exon shown in FIG. 1B, to the 3' untranslated region.

FIG. 3B shows the splicing donor/acceptor sites of the segment of cDNA shown in FIG. 3A.

DETAILED DESCRIPTION OF THE INVENTION

Membrane anchoring peptides are parts of the heavy chains of the associated isotypes and anchor the isotypes to the cell surface. For IgM, IgD and IgG respectively, these anchoring peptides have lengths of 41, 55, and 71 amino acids. These membrane anchoring peptides can be divided into three segments, each segment located differently with respect to the plasma membrane. The middle segments of 25 uncharged and hydrophobic residues are in the membrane lipid bilayer. The C-terminal hydrophilic segments of the membrane anchoring peptides of IgM and IgD have 3 residues, while the corresponding C-terminal hydrophilic segment of IgG has 28 residues. These C-terminal segments are proposed to be intracellular. The segments of IgM and IgD towards the N-terminus contain 13 and 27 amino acid residues respectively, whereas the corresponding segment of IgG contains 18 residues. These segments towards the N-terminus are highly acidic and hydrophilic and are therefore proposed to be on the extracellular surface of the plasma membrane. Because the N-terminus segments are probably extracellular, they are likely to be exposed and accessible to antibodies and can be targeted, thereby providing a means of destroying B cells producing a particular isotype. The migis epitopes are formed, in whole or in part, by these extracellular segments.

The proposed sequences of the membrane anchoring peptides of IgG (subclasses 1 to 4) were determined by the methods outlined below. The sequences of the membrane anchoring peptides of IgM and IgD were previously published, although, as discussed below, the published sequence of human IgM was shown to be partially incorrect by the inventors.

Peptides containing the extracellular migis epitopes, or segments or immunologic equivalents of these peptides, can be used as immunogens. Such immunogenic peptides can be synthesized by conventional techniques, such as with the RaMPS system (DuPont DeNemours & Co.), which applies Fmoc chemistry. Alternatively, recombinant peptides or immunoglobulin heavy chains (or portions thereof) containing the migis epitopes may be biosynthesized by expressing in *E. coli* or eukaryotic cells the gene segments containing the coding sequence of these peptides.

When using a synthetic peptide segment as an immunogen, it is usually more effective to conjugate it to a protein carrier, for example, hepatitis B surface antigen, core antigen, or preferably keyhole lympit hemocyanin (KLH). If the peptidic segment lacks a lysine residue or if the lysine residue is in the middle part of the segment, it is desirable to add a lysine residue at the C-terminal end. Because the N-terminus already has an α-amino group, the modified synthetic peptidic will have two available amino groups for linking.

Multiple molecules of peptides can be conjugated to each molecule of the carrier protein. With KLH, a preferred molar ratio for peptide/KLH is 10. The method of conjugation is very well established. Cross-linkers such as glutaraldehyde or bis (sulfosuccinimidyl) suberate or preferably disulfosuccinimidyl tartrate (Catalogue #21579, 20591, Pierce Chemical Co., Rockford, Ill.) can be used.

As immunogens, these peptides can be used to make monoclonal antibodies which are specific for them, using the protocol described further below. Specific examples of making monoclonal antibodies to the migis epitope of human ε chain appear in U.S. patent application Ser. No. 07/531,787, filed Jun. 1, 1990, and in U.S. patent application Ser. No. 07/468,766, filed on Jan. 23, 1990, the disclosures being incorporated herein by reference. The success in making monoclonal antibodies to an epitope on the ε chain extracellular migis segment, which is 15 amino acids in length, indicates that one should also be able to also make such antibodies to epitopes on the IgM, IgD or IgG extracellular migis segments, which are all of comparable length to the migis ε segment or are longer. The production of antibodies against this segment of human δ chain (IgD) has been reported. See Blattner, F. R. et al, Nature, 307:417-422 at 418 (1984).

The immunogenic peptides of the invention can also be used to immunize rabbits, goats, rats, or mice (or even another human being) to prepare polyclonal antibodies to the extracellular migis epitopes. Monoclonal antibodies that react with the peptides of the invention can be further screened for positive specific reactivity with cells bearing a specific isotype. The monoclonal antibodies can then be applied in vivo. Polyclonal antibodies made against peptides of the invention, however, generally contain almost entirely antibodies that react with the synthetic peptide but not the native molecules. Whether the polyclonal antibodies made against synthetic peptides can react with intact cells must be tested.

When preparing monoclonal antibodies, it is not necessary to use the synthetic or recombinant peptides in both immunization and antibody identification. For example, in immunizing mice for preparing spleen cells for fusion with myeloma cells, the immunogen may be the membrane-bound immunoglobulin isolated from the plasma membrane of immunoglobulin-bearing myeloma cells, such as IgG-expressing IM-9 cell line, or it may be the myeloma cells themselves. Transfectomas, which are developed by transfecting animal myeloma cells with genes of human immunoglobulin heavy chains and light chains and which express on their cell surface membrane-bound immunoglobulins, may also be used as immunogens. For initial monoclonal antibody identification following immunization, the aforementioned synthetic peptides conjugated to ovalbumin or bovine serum albumin, which are not used as carrier proteins in immunization, are preferably used.

Lymphocytes from the spleen or lymph nodes of immune mice and rats can also be used to prepare hybridomas secreting monoclonal antibodies specific for the extracellular migis epitopes. A preferred protocol for preparing monoclonal antibodies is to fuse immune spleen cells of mice with non-secreting mouse myeloma cells, such as NS-1 or SP2/0 cells, using polyethylene glycol.

A preferred immunization protocol for preparing monoclonal antibodies is to inject into each mouse 50 μg of the conjugate of KLH and the recombinant or synthetic peptides of the invention in complete Fruend's adjuvant. Two and four weeks later, the same amount of antigen is given subcutaneously in incomplete Fruend's adjuvant. After about six weeks, the fourth antigen injection is given intraperitoneally in saline. Mice are sacrificed 4 days after the last injection and the spleens are removed for preparing single cell suspensions for fusion with myeloma cells.

A similar protocol can be used for immunization with purified native human membrane-bound immunoglobulins (having attached membrane anchoring peptide segments) isolated from the plasma membrane of immunoglobulin-bearing human myeloma cells, such as IM-9 cells. When human immunoglobulin-bearing cells are used as the immunogen, $1 \times 10^7$ cells are injected intraperitoneally at two week intervals.

The fusion procedure with polyethylene glycol and other various procedures concerning cloning and hybridoma culturing have been well established. The preferred protocol is the well-known one described by Hudson, L. and Hay. F. C. (Practical Immunology, 2nd edition, pp. 303-313, 1980, Blackwell Publishing Co., Boston).

The screening of hybridomas for monoclonal antibodies (or the identification of polyclonal antibodies) reactive with the extracellular migis epitopes of the invention can be performed with an enzyme linked immunosorbent assay (ELISA) using the synthetic peptide as the solid phase antigen. A preferred solid phase antigen is the conjugate of a membrane anchoring peptide with a carrier protein different from that used in the immunogen, such as bovine serum albumin or ovalbumin. Monoclonal antibodies specific for the migis peptide of a particular isotype will then screened for specific binding to B cell lines and B cells expressing the particular isotypes by using immunofluorescence flow cytometric analyses.

Generally, the migis epitope-specific monoclonal antibodies which are first obtained will be murine-derived, and thus may be immunogenic or allergenic in human therapy. It is therefore desirable to produce chimeric antibodies (having an animal variable region and a human constant region), or to use human cDNA expression libraries (Stratagene Corp., La Jolla, Calif.) to produce fragments of human antibodies ($V_H$, $V_L$, $F_V$, Fd, Fab, or F(ab')$_2$) and then construct whole human antibodies using techniques similar to those for producing chimeric antibodies. In addition, one can create antibodies in which the entire constant portion and most of the variable region are human-derived, and, only the antigen binding site is mammalian derived. See Riechmann, L. et al., Nature 332:323-327 (1988). Further, one can create single peptide chain antibodies in which the heavy and light chain $F_v$ regions are connected. See Huston, J. S. et al., Proc. Natl. Acad. Sci. USA 85:5879-5883 (1983). All of the wholly and partially human antibodies are less immunogenic than mammalian equivalents, and the fragments and single chain antibodies are less immunogenic than whole antibodies. All these types of antibodies are therefore less likely to evoke an undesired immune or allergic response. It is noted that such an undesired immune response could bind and neutralize any antibodies of the invention which are administered before such antibodies can function to suppress the immune response.

Monoclonal antibodies specific for the extracellular migis epitopes of particular isotypes can be used to reduce or eliminate the B cells expressing these isotypes by antibody-dependent cellular cytotoxicity (ADCC), complement-mediated cytolysis, or other cytolytic or regulatory immune mechanisms. For example, antibodies of certain IgG subclasses, such as mouse IgG$_{2a}$ and human IgG$_1$ and IgG$_3$, can mediate ADCC carried out by certain Fc receptor-bearing phagocytic leukocytes. Administration of such mouse IgG$_{2a}$ antibodies, chimeric antibodies bearing human γ-1 or γ-3 chains, or human IgG$_1$ or IgG$_3$ antibodies can be used to target and down-regulate or lyse B cells of a particular isotype. These antibodies can be administered to suppress the immune system because they cause lysis of substantially all the B cells which express immunoglobulin of the targeted isotypic class, and consequently, they will reduce substantially all of such cells. The monoclonal antibodies of the invention can also be used as targeting agents for cytotoxic agents and cells.

The monoclonal antibodies of the invention can also be used as carrier agents for; cytotoxic drugs or for delivering an effector substance, by conjugating the monoclonal antibodies to these substances. A toxin-antibody conjugate will bind and directly kill B cells producing the isotypes IgM, IgD, or IgG, but not B cells producing other isotypes. These toxins are cytolytic or cytotoxic agents, including cytotoxic steroids, gelonin, abrin, ricin, Pseudomonas toxin, diphtheria toxin, pokeweed antiviral peptide, tricathecums, radioactive nuclides, and enzymes including membrane-lytic enzymes (such as phospholipase). The antibody and the agent can be conjugated by chemical or by genetic engineering techniques. The toxin-antibody conjugates may be used alone or in combination with the free antibodies of the invention.

The antibodies of the invention (and the toxin conjugates, fragments, and other derivatives) are administered systemically. It is preferable, at present, to administer them intravenously. They can be administered in any pharmaceutically acceptable vehicle. More than one antibody against one isotype can be administered at the same time. For example, different combinations of anti-migis-$\mu$, anti-migis-$\delta$ and anti-migis-$\gamma$ antibodies can be used simultaneously to achieve immuno-suppression.

Another therapeutic alternative involves active immunization, wherein antibodies specific to the $\mu$, $\delta$, or $\gamma$ chain migis epitopes are endogenously produced in vivo. These endogenously produced antibodies bind the migis epitopes and cause destruction of the associated B cells. Production of such antibodies can be induced either by administering a peptide including a migis epitope, or its immunological equivalent, or a paratope-specific, anti-idiotypic antibody. Anti-idiotype antibodies against the paratope of the antibodies of the invention conformationally resemble the extracellular migis epitopes. These anti-idiotypic antibodies can be used to actively immunize against the migis epitopes and induce the endogenous formation of antibodies against the migis epitopes.

Such paratope-specific, anti-idiotyptic antibodies are administered to a patient in an immunogenic amount sufficient to induce the formation of antibodies against B cells expressing IgM, IgD or IgG. These anti-idiotypic antibodies are preferably administered as chimeric antibodies or human antibodies, to minimize any immune response against them. They may also be any of the antibody fragments, $V_H$, $V_L$, $F_V$, Fd, Fab, or $F(ab')_2$ (which also may be chimeric or human in nature).

Certain factors, such as granulocyte monocyte-colony stimulation factor (GM-CSF) or monocyte-colony stimulation factor (M-CSF), are known to induce the proliferation of leukocytes, including those mediating ADCC. In in vitro experiments, GM-CSF and M-CSF have been shown to augment the ADCC activity on tumor cells mediated by monoclonal antibodies specific for surface antigens expressed on the tumor cells. The therapeutic effect of specific monoclonal antibodies of the invention, conjugates, or polyclonal antibodies in suppressing the immune response could perhaps be enhanced by combining them with factors that augment ADCC activities.

Derivative antibodies can be made which draw cytotoxic cells such as macrophages or cytotoxic T cells toward the targeted immunoglobulin-expressing B cells. These derivative antibodies include bi-specific antibodies having a specificity for a receptor of a cytotoxic cell and a specificity for the targeted Ig expressing B cells. Such hybrid bi-specific antibodies can include two different Fab moieties, one Fab moiety having antigen specificity for the targeted migis epitopes of the $\mu$, $\delta$, or $\gamma$ chains, and the other Fab moiety having antigen specificity for a surface antigen of a cytotoxic cell, such as CD3 or CD8. The bi-specific antibodies of the invention can be a single antibody having two specificities, or a heteroaggregate of two or more antibodies or antibody fragments. See, e.g., C. Reading, U.S. Pat. Nos. 4,474,893 and 4,714,681; Segal et al., U.S. Pat. No. 4,676,980.

While monoclonal antibodies of the invention can be used for in vivo applications, they may also be used in extra-corporeal ex-vivo applications. The IgM, IgD or IgG bearing B cells in the circulation of the patients can be removed by an affinity matrix (antibody immobilized on a solid phase) which is conjugated with the monoclonal antibodies of the invention.

Another use for the antibodies of the invention is for determining numbers and relative proportions of B lymphocytes bearing particular isotypes in mixed leukocyte populations. The migis specific antibodies will not react with cells which bear secreted immunoglobulins via such cells' Fc receptors. Such cells include macrophage and activated T cells. The profile of the B cells may indicate the immune status of the individual, and whether further suppression is desirable. The same information can also indicate how much antibody is needed to deplete a substantial portion of B cells bearing a particular isotype. For this purpose, antibodies can be used in standard assays which are used to determine cell surface antigens. In general, the antibodies are incubated with a sample of the leukocytes to be tested under conditions which allow the antibodies to bind isotype-bearing cells in the sample. The cells are then examined for binding of antibody. This can be accomplished by conventional cell staining procedures, for example, a fluorescently labeled second antibody can be used to detect binding of antibody.

A. Sequences of Migis Peptides of Human IgD and IgM

The sequence of the extracellular migis segments of human IgD membrane anchoring peptide was previously published as follows:

Human IgD  YLAMT.PLIPQ.SKDEN.SDDYT.TFDDV.GS

The sequence of the migis segment of human IgM was previously published by Rabbits, T. H. et al. Nucl. Acids Res. 9: 4509–4524 (1981), who indicated that it was the same as the corresponding segment of mouse IgM, which is as follows:

EGEVN.AEEEG.FEN

However, with the cDNA sequencing described below the sequence of the extracellular migis segment of human IgM was deduced to actually be:

Human IgM  EGEVS.ADEEG.FEN

The features and properties of the various segments of the whole human IgD and IgM membrane anchoring peptides are as shown below in Table I.

TABLE I

|  | First (N-terminal) Segment | Middle Segment | Last (C-terminal) Segment | |
|---|---|---|---|---|
| Properties: | Hydrophilic Highly Acidic | Hydrophobic No charged residues | Hydrophilic | |
| Physical Location: | On exterior surface | In membrane lipid bilayer | On cytoplasmic surface | Totals |
| Human IgM* | 13 | 25 | 3 | 41 |
| Human IgD* | 27 | 25 | 3 | 55 |

*The numbers represent the number of amino acid residues.

The nucleotide sequence in the membrane region of human μ mRNA was determined by the following procedure. Total mRNA was isolated from peripheral blood mononuclear cells of a normal donor, and from a human surface IgM-expressing cell line, RPMI-1788 (obtained from the ATCC, Rockville, Md.) according to the techniques described in Molecular Cloning, (Sambrook, Fritch, and Maniatis, Cold Spring Harbor, 1989). Two oligonucleotides were synthesized and used as the primers for PCR, based on the known DNA sequences published by Rabbitts, T. H. et al., Nucleic Acids Research 9: 4509–4514 (1981). These primers had the sequences:
5' end: 5'CCAACAGGGTCACCGAGAG3'
3' end: 5'CCTTGAACAAGGTGACGGT3' (complementary).
The amplified DNA product were cloned and the sequences of the gene setments for both the normal donor and the RMPI-1788 cells were determined to be: AG.GGG.GAG.GTG.AGC.GCC.GAC.GAG.-GAG.GGC.TTT.GAG.AAC. From this sequence, the amino acid sequence of the extracellular migis-μ segment (shown above) was deduced. The PCR conditions used were similar to those used in sequencing the migis-γ segments, discussed in Section B (ii) below.

B. Membrane Anchoring Peptides of Human γ Chain (i) Extracellular Migis-γ Segments The genomic DNA sequences of the membrane anchoring segments of human γ-1, γ-2, γ-3, γ-4, were determined by the methods described below. Two membrane exons encode for these DNA sequences. In FIGS. 1A, 1B, respectively, the genomic nucleotide sequences corresponding to the two membrane exons of human γ-1 are underlined. The upper case letters in FIG. 2A denote the genomic DNA sequence of these two membrane exons for human γ-1, γ-2, γ-3, and γ-4, the flanking nucleotide sequences being indicated by lower case letters. FIG. 2B shows the deduced amino acid sequences encoded by the exons of FIG. 2A. FIG. 3A shows the DNA sequence of a gene segment of human γ-1 chain which includes the two membrane exons and some flanking sequences. FIG. 3B depicts the splicing donor sites and acceptor sites involved in the formation of the segment shown in FIG. 3A.

Based on the genomic DNA sequences, mRNA sequences, and the identified splicing mechanisms, the predicted amino acid sequences of the membrane anchoring peptides of human γ-1, γ-2, γ-3, and γ-4 shown in FIG. 2B were determined. By comparing to the sequences of membrane anchoring peptides of other known immunoglobulins, the hydrophobic stretch that presumably spans through the membrane lipid bilayer can be identified. This sequence of 25 amino acid residues is LWTTI.TIFIT.LFLLS.VCYSA.TVTFF. To the N terminal end of this hydrophobic stretch is the segment proposed to form the migis segment. Thus for all human γ chains, the sequence of 18 amino acid residues (as shown in FIG. 2B) which form the extracellular migis segment, entirely or in part, is:

ELQLE.ESCAE.AQDGE.LDG.

These proposed migis segments are believed to be extracellular and accessible by antibodies, based on the fact that they have multiple acidic residues, which suggests that they are hydrophilic. Since the migis segments for human γ-1, γ-2, γ-3, and γ-4 are identical, it is likely a monoclonal antibody can be prepared which recognizes cell-bound but not secreted IgG of any of the four subclasses.

(ii) Sequencing the Human migis-γ Segment

The proposed sequence of the membrane anchoring peptides of human γ chains was determined by the methods set forth below. The genomic DNA clones containing γ-1, γ-2, γ-3, and γ-4 can be obtained from a genomic DNA library, such as γ.FIX phage library of genomic DNA of human lung fibroblast line, WI38, provided by Strategene (LaJolla, Calif.). The human genomic γ-1, γ-2, γ-3, and γ-4 DNA segments, which were originally provided by Dr. Sherrie Morrison (previously of Columbia University and now of the University of California, Los Angeles), were used for constructing chimeric murine $V_H$/human $C_\gamma$ genomic DNA. The human B cell line, IM9, expressing IgG$_1$ on the surface was obtained from the American Type Culture Collection, Rockville, Md. Peripheral blood mononuclear cells from normal blood donors were used as a source of mRNA for examining human γ chain sequences. The various restriction enzymes used were from Boehringer Mannheim, New England Biolabs and Bethesda Research Laboratories. The Erase-a-base kit, which can be used to construct nested deletions, was obtained from Promega Corp. Dideoxysequencing of double stranded templates was performed using T7 sequencing kit from Pharmacia/LKB. The Bluescript vector was obtained from Strategene Cloning Systems. All the host cells were DH5αF' cells (Bethesda Research Laboratory).

To facilitate mapping and sequencing, the genomic γ clones were subcloned into Bluescript SK II+. In order to locate the membrane regions, a set of the nested deletions was created using the Erase-a-base kit. The γ plasmid was cut with SacI and NcoI. SacI gives 5' recessed ends which are protected from Exo III digestion. Several μg of plasmid were digested with Exo III and aliquot were withdrawn at 30 second intervals. These aliquot were placed in S1 digestion mix, which stops the Exo III reaction. After 30 minutes, the S1 reaction was stopped by heating to 70° C. Following a brief treatment with Klenow polymerase; each Eragment; was recircularized with T4 DNA ligase. Plasmids with deletions of various lengths were sequenced and compared to mouse γ chain membrane regions. After identifying clones which contain a part of the membrane regions, oligonucleotide primers were constructed to complete the sequencing of segments covering the membrane exons.

For sequencing cDNA, the cDNA clones were prepared from cDNA synthesized from RNA isolated from IM9 cells or peripheral blood mononuclear cells from normal donors, by using a primer in the 3'untranslated region 5'GTTGAGGGCGGTGAGACG3' (complementary sequence determined from genomic DNA) of IM9 cells and AMV reverse transcriptase. The RNA isolation and cDNA preparation were performed according to *Molecular Cloning*, (Sambrook, Fritch, and Maniatis, Cold Spring Harbor, 1989). Second strand synthesis and amplification of desirable gene segments was carried out using PCR with a 3' primer, 5'GGCAACTGCGAGGCCAGAG3' from the 3' untranslated region and a primer with the sequence from the CH3 domain (5'AGAAGAGCCTCTCCCTGTC3'). The PCR conditions were as follows: denaturation, 94° C., 1 min; annealing, 60° C., 2 min; polymerase reaction, 72° C., 3.5 min; 35 cycles.

Two bands of 350 and 500 nucleotide were isolated from IM9 RNA source. These were cloned into Bluescript SK II+. Upon sequencing, clones with 350 bp inserts having γ-1 sequences were identified. This cDNA was labeled with $^{32}P$ and used to screen by colony hybridization a number of cDNA clones derived from the PCR product of RNA from normal lymphocytes. The inserts of the positive clones were prepared and the nucleotide sequences determined.

F. Developing Monoclonal Antibodies Against migis Epitopes

The determination of nucleotide sequences of genomic and cDNA segments covering the membrane exon regions of the various isotypes of human heavy chains described above has provided the deduced amino acid sequences of the extracellular segments of the membrane anchoring peptides of the membrane-bound heavy chains. Synthetic or recombinant peptides with sequences representing the extracellular migis segments of the membrane anchoring peptides can be used to develop murine monoclonal antibodies against the migis epitopes using the standard techniques described above and/or the methods described in U.S. patent application Ser. Nos. 07/531,787 and 07/468,766.

It should be understood that the foregoing embodiments, procedures and products are exemplary only and not limiting, that the scope of protection is defined only in the following claims, and that it includes all equivalents of the subject matter of those claims.

What is claimed is:

1. A monoclonal antibody or antigen binding fragment thereof which binds to a peptide segment represented by the sequence.

EGEVS.ADEEG.FEN.

2. The monoclonal antibody of claim 1 which is a chimeric antibody having animal variable regions and human constant regions.

3. The chimeric antibody of claim 2 wherein said chimeric antibody has murine variable regions and human constant regions.

4. The antibody of claim 1 having all of its complementarity determining regions from an animal and its constant region from a human.

5. A hybridoma cell line which produces a monoclonal antibody or fragment of claim 1.

6. A continuous, stable cell line which produces a chimeric antibody of claim 2 or 3.

7. The cell line of claim 6 which is a transfectoma.

8. A monoclonal antibody or antigen binding fragment thereof which binds to a peptide segment represented by the sequence ELQLE.ESCAE.AQDGE.LDG.

* * * * *